US010623380B1

(12) United States Patent
Pratt et al.

(10) Patent No.: US 10,623,380 B1
(45) Date of Patent: Apr. 14, 2020

(54) SECURE TRANSFER OF MEDICAL RECORDS TO THIRD-PARTY APPLICATIONS

(71) Applicant: CERNER INNOVATION, INC., Kansas City, KS (US)

(72) Inventors: Douglas Charles Pratt, Kansas City, KS (US); Amaresh Vakul Vakulabharanam, Kansas City, KS (US)

(73) Assignee: Cerner Innovation, Inc., Kansas City, KS (US)

(*) Notice: Subject to any disclaimer, the term of this patent is extended or adjusted under 35 U.S.C. 154(b) by 279 days.

(21) Appl. No.: 15/857,937

(22) Filed: Dec. 29, 2017

(51) Int. Cl.
| | |
|---|---|
| *H04L 9/00* | (2006.01) |
| *H04L 29/06* | (2006.01) |
| *G06F 21/44* | (2013.01) |
| *G06F 21/62* | (2013.01) |
| *G16H 10/60* | (2018.01) |
| *G16H 80/00* | (2018.01) |
| *G06F 21/60* | (2013.01) |

(52) U.S. Cl.
CPC .......... *H04L 63/0428* (2013.01); *G06F 21/44* (2013.01); *G06F 21/604* (2013.01); *G06F 21/6245* (2013.01); *G16H 10/60* (2018.01); *G16H 80/00* (2018.01); *G06F 2221/2115* (2013.01)

(58) Field of Classification Search
CPC ... H04L 63/0428; G06F 21/604; G06F 21/44; G06F 21/6245; G16H 10/60; G16H 80/00
See application file for complete search history.

(56) References Cited

U.S. PATENT DOCUMENTS

| | | | |
|---|---|---|---|
| 8,898,798 B2 | 11/2014 | Rogers et al. | |
| 9,414,776 B2 | 8/2016 | Sillay et al. | |
| 2012/0129485 A1* | 5/2012 | Hebbar | H04L 9/083 455/404.1 |

(Continued)

OTHER PUBLICATIONS

Apixio HCC Profiler Brochure, "Reimagining Risk Adjustment", Apixio.com, May 26, 2017. Available at: https://www.apixio.com/wp-content/uploads/2016/02/Apixio_HCC_Profiler_Brochure_052617.pdf.

*Primary Examiner* — Beemnet W Dada
(74) *Attorney, Agent, or Firm* — Shook, Hardy & Bacon L.L.P.

(57) ABSTRACT

Media and methods for securely providing third-party applications, such as health based service applications, with electronic medical records (EMRs), or discrete information therein, of an individual is provided. To facilitate the secure transfer of medical records, a universal security manager is described. The universal security manager may act as an intermediary between a healthcare service facility, such as a hospital, and the third-party application. A secure link for transferring EMRs from the healthcare service facility to the universal security manager may be established using a secure linking code. The third-party application may be validated as a trusted third-party application by the universal security manager based on a set of security criteria. The universal security manager may provide the EMR information from an EMR system associated with the healthcare service facility to the trusted third-party application based on a set of permissions created and/or maintained by a user.

20 Claims, 3 Drawing Sheets

(56) References Cited

U.S. PATENT DOCUMENTS

| | | | |
|---|---|---|---|
| 2013/0054271 A1* | 2/2013 | Langford | G06Q 50/24 |
| | | | 705/3 |
| 2014/0067425 A1* | 3/2014 | Dudar | G06F 19/3468 |
| | | | 705/3 |
| 2016/0042483 A1* | 2/2016 | Vo | G16H 10/60 |
| | | | 705/3 |
| 2017/0011174 A1* | 1/2017 | Higgs | H04L 67/10 |
| 2018/0032684 A1* | 2/2018 | Raja | G06F 19/3475 |

* cited by examiner

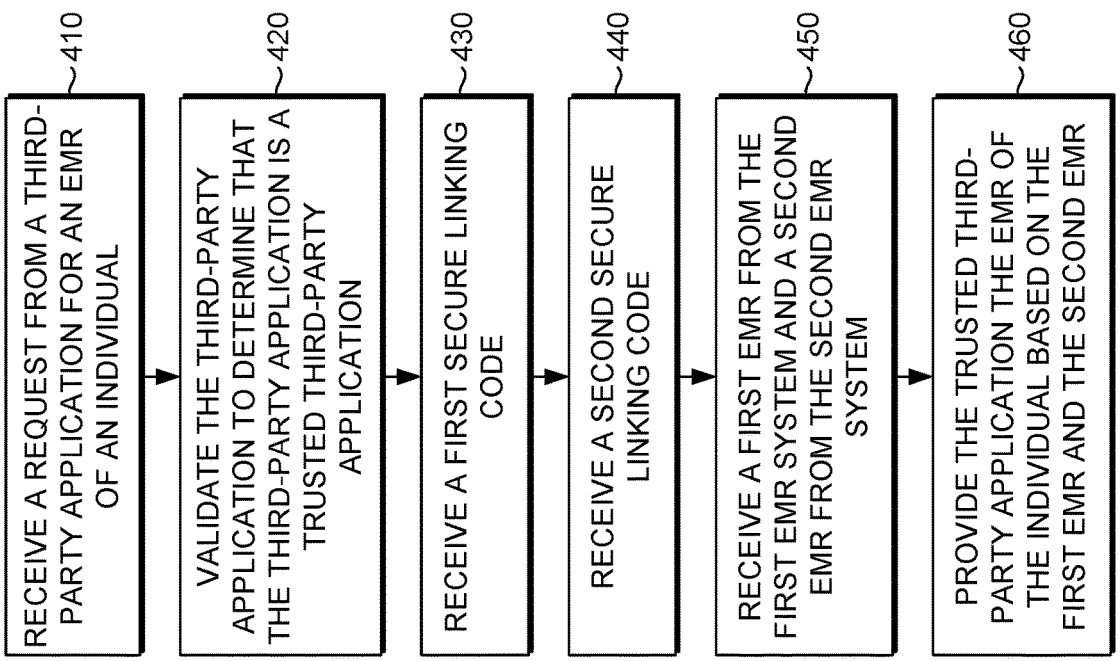

SECURE TRANSFER OF MEDICAL RECORDS TO THIRD-PARTY APPLICATIONS

BACKGROUND

The rise of mobile technology and application-based software programs has created a greater demand for sharing medical information. For instance, numerous third-party applications have flooded the marketplace and offer users a service or benefit. Many of these application-based technologies provide health related services, such as tracking and recommending diets, tracking and recommending physical exercise routines, tracking sleep patterns, and tracking reproductive patterns. The number of health based applications goes on and on, and is continually growing larger by the day.

Parallel to the growth in application based health services, the use of electronic medical record (EMR) technology skyrocketed as well. During the 2000's and continuing on, health service facilities have made the move from paper based health records to wholly electronic EMR systems. Some of these EMR systems were not compatible with other EMR systems, which varied from health service facility to health service facility. While a large part of this transition was due to market demand and the increased benefit of EMR systems, much of the transition occurred in response to government regulations and laws that require the adoption of EMR systems.

The transition of health service facilities to EMR systems opened up a new door for health related applications to increase their value based health services by accessing EMRs of individuals. One of the problems with this, however, is that EMR information is some of the most private and personal information related to an individual. For instance, most EMR information includes not only health information, such as diagnoses, medical procedures, and lab results, but also includes personal identifying information, such as names, dates of birth, social security numbers, and so forth. Therefore, this information is increasingly protected and regulated. The increasing protection and regulation regarding EMRs makes it more difficult for application-based health services to access information that is beneficial to the individual consuming the service.

The increasing regulation afforded to EMRs and the increased adoption of EMR systems created a technological problem for application-based health services: The use of various types of EMR systems, some of which are incompatible with each other, led to the inaccessibility of some or all EMR information. Further problems relate to an individual's right to access EMRs and provide their EMRs to these third-party applications, which includes the right to transfer only a selected amount or type of healthcare information. One of the technological challenges that resulted from the rise of application-based health services and the increased adoption of EMR systems, which sometimes includes various types of EMR systems, is the secure transfer of EMRs to application-based health services in a manner that is controlled by the individual.

Conventional methods attempt to address this problem by directly transferring EMRs from healthcare service facilities to third-party applications. However, this method fails in several respects. Here, a user must individually authorize each healthcare service facility to release records to the third-party application. This also includes establishing a user account at each third-party application, which sometimes includes establishing a separate account at a single third-party application for different healthcare service facilities. Then, after having set up the accounts between the various entities, the user is removed from the transfer process, since this occurs directly between the healthcare service facility and the third-party application.

SUMMARY

The present technology generally relates to the secure transfer of EMRs, or discrete information therein, to third-party applications. As used herein, EMR refers generally to the entirety of an EMR or discrete pieces of information therein. More specifically, some aspects of the technology describe a universal security manager that may be used as an intermediary for transferring medical information between one or more healthcare service facilities, such as a hospital, and one or more third-party applications, such as a health based mobile application. In some cases, a secure linking code is used to establish a link for transferring information between the one or more healthcare service facilities and the universal security manager, which in some cases includes EMR systems that are incompatible. In some cases, the universal security manager validates the third-party application to determine if the application is a trusted third-party application, for example, based on meeting a minimum set of security criteria. The universal security manager may enable the transfer of the information to the trusted third-party application based on the validation. In some aspects, a user of the universal security manager, for example, an individual patient, may create a set of preferences that set parameters on transferring EMRs, or information therein, from the healthcare service facility to the trusted third-party application.

As previously discussed, one of the technological challenges resulting from the rise of application-based health services and the increased adoption of EMR systems is the secure transfer of EMRs (or the information therein) from various types of EMR systems to third-party applications in a manner that is controlled by the individual.

The present disclosure and its subsequent claims provide a solution for the technological problem of securely transferring medical records or portions thereof. In some of the embodiments, the universal security manager enables secure links for transferring at least a portion of EMR information from multiple types of EMR systems to the universal security manager. In this way, the universal security manager is considered "universal." In some cases, the secure link may be established using a linking code received in response to an interaction of an individual with a healthcare service facility. By using the linking code in this example, electronic security is improved over conventional systems because of the higher probability that the user is permitted to receive and/or direct EMRs for the individual patient.

In some aspects, the problem is further solved by validating a third-party application based on a set of minimum security criteria, which may be set by a healthcare service facility, an EMR provider, a user, and/or a rulemaking authority. Thus, validating the third-party application prior to transferring EMRs increases the security for transferring EMR information from a healthcare service facility. In some cases, this may include transferring EMR information from one or more healthcare service facilities having one or more EMR types.

Additionally, unlike the conventional methods described above, a user of a universal security manager may remain in control of the secure EMR information transfer process because some aspects of the technology allow the user to create and maintain parameters, or permissions. These permissions may be stored as rules that direct the transfer of medical records from one or more healthcare service facilities to one or more trusted third-party applications in the manner prescribed by the user.

Accordingly, one aspect of the technology provides for one or more non-transitory computer storage media having computer-usable instructions stored thereon, that when executed by a processor, cause the processor to perform a method for establishing a universal security manager for providing a third-party application with electronic medical records (EMRs) (or other personal records) of an individual. The method comprises: receiving a request from the third-party application for a first EMR, the first EMR stored on a first EMR system; validating the third-party application to determine that the third-party application is a trusted third-party application; receiving a first secure linking code, the first secure linking code generated at the request of a first service facility associated with the first EMR system, wherein the first secure linking code is generated in response to a first interaction of the individual with the first service facility; based on receiving the first secure linking code, receiving the first EMR from the first EMR system; and providing the trusted third-party application with the first EMR.

In another aspect of the technology, a computer-implemented method for establishing a universal security manager for providing a third-party application with EMRs of an individual is provided. The method comprises: at one or more processors, receiving a request from the third-party application for a first EMR, the first EMR stored on a first EMR system; at the one or more processors, validating the third-party application to determine that the third-party application is a trusted third-party application; at the one or more processors, receiving a first secure linking code, the first secure linking code generated at the request of a first service facility associated with the first EMR system, wherein the first secure linking code is generated in response to a first interaction of the individual with the first service facility; at the one or more processors, based on receiving the first secure linking code, receiving the first EMR from the first EMR system; and by the one or more processors, providing the trusted third-party application with the first EMR.

Yet another aspect of the technology provides for one or more non-transitory computer storage media having computer-usable instructions stored thereon, that when executed by a processor, cause the processor to perform a method for establishing a universal security manager for providing a third-party application with EMRs of an individual. The method comprises: receiving a request from the third-party application for an EMR of the individual; validating the third-party application to determine that the third-party application is a trusted third-party application; receiving a first secure linking code, the first secure linking code generated at the request of a first service facility associated with a first EMR system, wherein the first secure linking code is generated in response to a first interaction of the individual with the first service facility; receiving a second secure linking code, the second secure linking code generated at the request of a second service facility associated with a second EMR system, wherein the second secure linking code is generated in response to a second interaction of the individual with the second service facility; based on receiving the first linking code and receiving the second linking code, receiving a first EMR from the first EMR system and a second EMR from the second EMR system; and providing the trusted third-party application the EMR of the individual based on the first EMR and the second EMR.

Additional objects, advantages, and novel features of the technology will be set forth in part in the description which follows, and in part will become apparent to those skilled in the art upon examination of the following or learned by practice of the technology.

BRIEF DESCRIPTION OF THE DRAWINGS

The present technology is described in detail below with reference to the attached drawing figures, wherein:

FIG. 3 is a block diagram of an example method for establishing a universal security manager, in accordance with aspects described herein; and FIG. 4 is a block diagram of another example method for establishing a universal security manager, in accordance with aspects described herein.

DETAILED DESCRIPTION

The subject matter of the present technology is described with specificity herein to meet statutory requirements. However, the description itself is not intended to limit the scope of this disclosure. Rather, the inventors have contemplated that the claimed or disclosed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

In brief and at a high level, some aspects of the technology describe a universal security manager that may be used as an intermediary for transferring EMR information between one or more healthcare service facilities and one or more third-party applications. In some cases, a secure linking code is used to establish a link for transferring EMR information between a healthcare service facility and the universal security manager. In some cases, the universal security manager validates the third-party application based on the third-party application meeting a minimum set of security criteria to determine if the application is a trusted third-party application. The universal security manager may enable the transfer of EMR information to the trusted third-party application based on the validation. In some aspects, a user of the universal security manager may create parameters for transferring EMR information from the healthcare service facility to the trusted third-party application. In some cases, EMR information from one or more EMR systems may be altered based on the parameters before sending the EMR information to the trusted third-party application.

Figure 1:
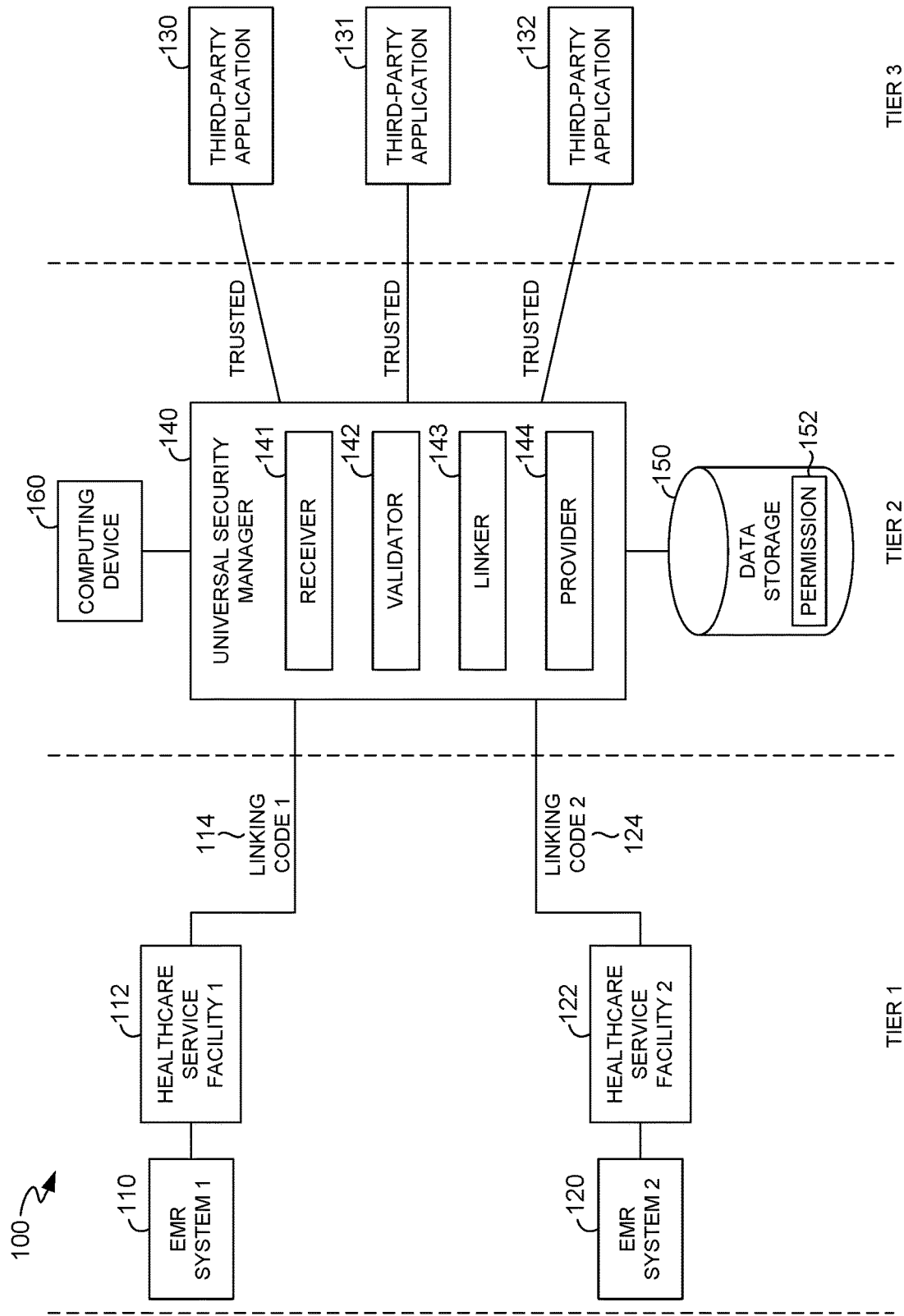
FIG. 1 is an example operating environment having an example universal security manager, in accordance with aspects described herein.

With reference now to FIG. 1, an example operating environment 100 having an example universal security manager 140 is illustrated. It will be understood that example operating environment 100 and universal security manager 140 are provided as examples of embodiments suitable for practicing the technology. Other arrangements of components (e.g., machines, interfaces, functions, orders, and groupings of functions, etc.) can be used in addition to or instead of those shown, while some may be omitted from FIG. 1 for the sake of clarity.

Having this in mind, example operating environment 100 of FIG. 1 is shown having EMR system 1, 110, healthcare service facility 1, 112, and linking code 1, 114. FIG. 1 also comprises EMR system 2, 120, healthcare service facility 2, 122, and linking code 2, 124. As shown in FIG. 1, each of these is illustrated as within Tier 1. Tier 2 of FIG. 1 is illustrated as having universal security manager 140, data storage 150, and computing device 160. And Tier 3 of FIG. 1 is illustrated as having a plurality of third-party applications 130-132. The Tiers 1-3 are provided only for ease in explaining an example of the technology, and to further illustrate the need for a universal security manager that is an intermediary (e.g., Tier 2) between EMRs of Tier 1 and third-party applications in Tier 3. The Tiers are not meant to imply a certain arrangement or distribution of components. For instance, in some cases, a universal security manager may be owned and/or operated by a healthcare service facility or an EMR/personal record provider. Thus, somewhat blurring the lines between the various Tiers.

As a general matter, a healthcare service facility, such as healthcare service facility 1, 112, and healthcare service facility 2, 122, may be any facility, temporary or permanent, utilized by individuals for obtaining a medical related service. For example, this may include permanent healthcare service facilities, such as hospitals, out-patient surgical centers, doctors' offices, physical and occupational therapy buildings, nursing homes, assisted living centers, and the like. In some cases, healthcare service facilities may be temporary, such as medical tents, mobile medical vehicles, at-home nursing care, ambulatory care, and the like. While only some examples have been provided to describe the general nature of a healthcare service facility, the scope of this disclosure is not intended to be limited to only these examples.

In some cases, a healthcare service facility may be associated with one or more EMR systems. EMR systems, such as EMR system 1, 110, and EMR system 2, 120, generally store EMRs of patients associated with one or more healthcare service facilities, such as healthcare service facility 1, 112, and healthcare service facility 2, 122, respectively. EMRs may comprise electronic clinical documents such as images, clinical notes, orders, summaries, reports, analyses, information received from clinical applications and medical devices, or other types of electronic medical documentation relevant to a particular patient's condition and/or treatment. Electronic clinical documents (such as EMRs) contain various types of information relevant to the condition and/or treatment of a particular patient and can include information relating to, for example, patient identification information, images, alert history, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, clinician assignments, and a host of other relevant clinical information.

The content and volume of such information in an EMR system are not intended to limit the scope of the present disclosure in any way. Further, though illustrated as a single, independent component, EMR systems may, in fact, include a plurality of applications and/or storage devices such as, for instance, a database cluster. In some cases, an EMR system may be associated with a healthcare service facility, in that the healthcare service facility contracts with an EMR system provider that may create and maintain the EMR system for the healthcare service facility.

EMR systems are generally not limited to only one type of EMR system. For instance, one healthcare service facility may use one type of EMR system, while another healthcare service facility may use a different type of EMR system. For example, with reference to FIG. 1, EMR system 1, 110, and EMR system 2, 120, may be different types of EMR systems. In some cases, they may be the same type of EMR system. These various scenarios may occur because there are different providers of EMR systems that healthcare service facilities may utilize, and in some instances, an EMR system may be unique to a particular healthcare service facility.

In any event, some of the various EMR systems will be compatible with other EMR systems, while some EMR systems will be incompatible. In some cases, what is meant by compatible or incompatible is whether data may be easily compared and/or shared between EMR systems. In one example, two EMR systems having the same or similar metadata tags for healthcare events may be compatible in that the EMR systems may easily compare and share data. In another example, two EMRs systems having different types of metadata tags for the same or similar healthcare events may be incompatible. In such cases, where EMR systems are incompatible, processing of the healthcare data from one or both of the EMR systems may occur in order to compare or share healthcare data.

Still with reference to FIG. 1, a plurality of third-party applications 130-132 is illustrated in Tier 3. In general, a third-party application, such as third-party application 130, may be any piece of software configured to be executed by a computing device. In some cases, a third-party application may be a desktop application, a mobile application, a web-based application, or the like. A third-party application may be owned and maintained by an entity other than a universal security manager, a healthcare service facility, or an EMR provider. However, nothing restricts a third-party application from being owned or maintained by the universal security manager, the healthcare service facility, and/or the EMR provider.

In some cases, a third-party application may wish to access EMRs of one or more individuals, also referred to as patients. In some cases, it may be beneficial for individuals to allow the third-party application to access their EMR information, or at least a portion of their EMRs, as the third-party application may provide a service desired by the individual. As an example, some third-party applications may include applications associated with health insurance companies, life insurance companies, home alarm and security companies, dietary and meal planning advice, physical and mental health advice, other healthcare service facilities, and the like. With reference to FIG. 1, each third-party application 130, 131, and 132 may wish to access at least a portion of an individual's EMR, which may be stored on EMR system 1, 110, and/or EMR system 2, 120. In some cases, third-party applications 130-132 may access all of or portions of an individual's EMRs through universal security manager 140.

With continued reference to FIG. 1, example universal security manager 140 is described. As illustrated, example universal security manager 140 is shown having receiver 141, validator 142, linker 143, and provider 144. It will be recognized that functions are described as being performed by one or more entities, which may be carried out by hardware, firmware, and/or software. It should be understood that this and other arrangements described are only provided as examples. Other arrangements and elements (e.g., machines, interfaces, functions, orders, and groupings of functions, etc.) can be used in addition to or instead of those shown, and some elements may be omitted altogether for the sake of clarity. Further, many of the elements described herein are functional entities that may be implemented as discrete or distributed components or in conjunction with other components, and in any suitable combination and location. For instance, some functions may be carried out by a processor executing instructions stored in memory. An example computing device suitable for performing aspects of this technology is provided and further described with reference to FIG. 2.

In some cases, functions performed by universal security manager 140 are associated with one or more virtual assistant applications, services, or routines. For example, such applications, services, or routines may operate on one or more user devices (such as computing device 160) and servers, and may be shared or distributed across one or more user devices and servers, one or more other components, or be implemented in the cloud. Moreover, the functions performed, or services carried out by these functions, may be implemented at appropriate abstraction layer(s) such as the operating system layer, application layer, hardware layer, and the like of the computing system(s).

In some cases, the functions and/or the embodiments described herein can be performed, at least in part, by one or more hardware logic components, which may be stored in data storage 150. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. In general, the logic comprises rules, conditions, associations, classification or prediction models, pattern inference algorithms, or other criteria utilized by universal security manager 140 to execute functions. In some embodiments, the logic may utilize pattern recognition, fuzzy logic, neural network, finite-state machine, support vector machine, logistic regression, clustering, or machine learning techniques, similar statistical classification processes, or combinations of these processes.

In some aspects of the technology, such as the one illustrated by FIG. 1, universal security manager 140 may communicate with one or more healthcare service facilities, such as healthcare service facilities 112 and 122. As illustrated, universal security manager also communicates with one or more third-party applications, such as third-party applications 130, 131, and 132. Universal security manager 140 may also communicate with data storage 150 and computing device 160. In some cases, universal security manager 140, and its associated functions, may be executed by computing device 160. In some cases, universal security manager 140 may communicate with these components directly or indirectly through a communication bus and/or through a network. The network may include, without limitation, one or more local area networks (LANs) and/or wide area networks (WANs). In example implementations, the network comprises the Internet and/or a cellular network, amongst any of a variety of possible public and/or private networks.

Data storage 150 generally stores information including data, computer instructions (e.g., software program instructions, routines, or services), and/or models used in embodiments of the technologies described herein. In an embodiment, data storage 150 comprises computer data memory. Further, although depicted as a single component, data storage 150 may be embodied as one or more data stores or may be in the cloud. As shown in FIG. 1, data storage 150 stores one or more permissions 152, which is described below in more detail.

Continuing with the description of example universal security manager 140 of FIG. 1, receiver 141 generally receives information from one or more components or entities. In some cases, receiver 141 may receive information in response to a request for information sent to the one or more components. Receiver 141 may receive information from one or more components so that the information may be used by other functional entities of universal security manager 140. As described above, receiver 141 may receive information by way of being communicatively coupled to the one or more components, such as by a bus and/or a network.

In some cases, receiver 141 may receive EMR information or portions of EMRs from one or more healthcare service facilities, such as healthcare service facility 1, 112, and/or healthcare service facility 2, 122. In some cases, receiver 141 may receive EMR information or portions of EMRs, directly or indirectly from an EMR system, such as EMR system 1, 110, and EMR system 2, 120, of FIG. 1. In some cases, receiving EMRs from an EMR system may comprise receiving the EMR information from an EMR system provider, not illustrated in FIG. 1 for the sake of clarity. In some cases, receiver 141 receives requests for EMRs from one or more third-party applications, such as from third-party application 130, 131, and/or 132.

In some cases, receiver 141 may receive information from computing device 160. Such information may be associated with a user of computing device 160. While computing device 160 is further described with reference to FIG. 2, in one example, the user may provide information to computing device 160 through a graphical user interface of computing device 160. Receiver 141 may receive the information provided by the computing device 160 by the user, so that the information may be utilized by other functions of universal security manager 140, or stored in data storage 150. In some cases, receiver 141 may receive information from data storage 150. Receiver 141 may receive information from other sources, such as the Internet. For example, via the Internet, receiver 141 may receive information related to minimum security standards for third-party applications when handling EMR information, as they are defined by a rulemaking authority.

Further illustrated as part of universal security manager 140 of FIG. 1 is validator 142. In general, validator 142 determines whether a third-party application, such as third-party application 130, 131, and/or 132, is a trusted third-party application. In some cases, validator 142 may determine that a third-party application is a trusted third-party application by determining that the third-party application meets a set of security criteria. To do so, information may be received from a third-party application regarding the third-party application's security standards. For instance, this information may be received by receiver 141. The third-party application security standards may comprise the security protocols that are implemented by the third-party application to protect information. For example, the third-party application may protect data by securing it on servers or data stores that require passcodes to access, by establishing firewalls, by contracting with cloud services that meet certain security protocols, by encrypting data, or by implementing other security technologies known or developed in the art.

Validator 142 may compare the third-party application's security standards to a set of security criteria. In some cases, the set of security criteria may be a minimum set of security criteria for determining that a third-party application is a trusted third-party application. The set of security criteria may be defined by a user; a universal security manager; a healthcare service facility; an EMR system provider; a rulemaking authority, such as a local, state, or federal governing authority; and/or another entity. Put another way, one or more minimum sets of security criteria for determining that a third-party application is a trusted third-party application may be defined by the user, the universal security manager, the healthcare service facility, the EMR system provider, and the rulemaking authority.

For example, the minimum set of security criteria may be determined by the user, e.g., an indication is received that the user authorizes a particular third-party application to receive EMR information. In another example, the healthcare service facility and/or the EMR system provider may define the minimum set of security criteria for a third-party application in order for the healthcare service facility and/or the EMR system provider to provide EMRs to the third-party application through the universal security manager, such as universal security manager 140 of FIG. 1. In yet another example, a rulemaking authority, such as Congress, may define a minimum set of security criteria for a third-party application to receive EMR information.

Upon comparing a third-party application's security standards to a set of security criteria, validator 142 may determine that the third-party application's security standards meet or exceed the set of security criteria. In some cases, based on determining that the third-party application's security standards meet or exceed the set of security criteria, validator 142 may validate the third-party application as a trusted third-party application. Validating the third-party application may comprise storing, for example in data storage 150, information that the third-party application has been determined to be a trusted third-party application. For example, this information may be accessed by other components of universal security manager 140 to facilitate the secure transfer of EMR information or portions of EMRs to the trusted third-party application. As such, a trusted third-party application may be a third-party application that has been validated and may receive all or portions of EMRs from a universal security manager.

Still with reference to universal security manager 140 of FIG. 1, universal security manager 140 is also depicted as comprising linker 143. In general, linker 143 establishes a link for receiving EMRs, for example, which may be received by receiver 141 in manners previously described. Linker 143 may utilize a linking code, such as linking code 1, 114, and linking code 2, 124, in FIG. 1. A linking code may be a secure linking code generated upon request of a healthcare service facility. The secure linking code may be generated by the healthcare service facility or may be generated by a contract service associated with the healthcare service facility, which in some cases, may be owned or operated by the universal security manager.

In some cases, a linking code may be generated in response to an interaction of an individual, i.e., a patient, with a healthcare service facility. For example, the interaction of the individual may be a physical interaction of the individual with the healthcare service facility. A physical interaction may comprise the individual visiting a location of the healthcare service facility and receiving a service from the healthcare service facility.

As an example, an individual may visit a doctor's office for a routine physical. The patient receives several services in this example: There may be an interaction with a front-desk staff that provides check-in and check out services; there may be an interaction with clinical support staff such as nurses, medical assistants, and x-ray technicians; there may be an interaction with a physician or mid-level provider; there may be an interaction with a laboratory technician that performs ordered tests, such as drawing blood; and so forth. Each of these services, either individually or as a whole, may be considered an interaction by the individual with the doctor's office.

In some cases, an interaction may comprise a non-physical interaction with a healthcare service facility. For example, an individual may call, email, text, etc. a healthcare service facility in order to provide or inquire about information. This too, in some cases, may be considered an interaction of an individual with the healthcare service facility.

In some cases, a linking code may be a unique character string. The unique character string may be based on an interaction of an individual with a healthcare service facility and a type of EMR system associated with the healthcare service facility. Using FIG. 1 as an example, linking code 1, 114, may comprise a unique string of characters of any length. The unique string may be based on an individual's interaction with healthcare service facility 1, 112, and the type of EMR system 1, 110. In some cases, this may mean that the unique string of characters provides for or includes, whether explicit or encrypted, information related to the interaction and the type of EMR system. In some cases, a universal security manager may not receive EMRs from a healthcare service facility and/or an EMR system until the universal security manager receives a linking code.

It will be understood that, in some cases, linking codes generated at the requests of different healthcare service facilities may comprise different unique character strings. For example, using FIG. 1, linking code 1, 114, and linking code 2, 124, may comprise different unique character strings. In some cases, this is because a type of EMR system 1, 110, is different than a type of EMR system 2, 120. As such, the unique character strings for linking code 1, 114, and linking code 2, 124, may be different because each conveys different information, and may be used to establish a different link for transferring EMRs, such as a link with healthcare service facility 1, 112, and healthcare service facility 2, 122, respectively.

In some cases, different linking codes may be received by a universal security manager, where the different linking codes are generated at the request of different healthcare service facilities, which may have different types of EMR systems. Thus, the different healthcare service facilities may store different EMR information for a single individual on their respective EMR systems. In some cases, these EMR systems are incompatible. As such, the universal security manager is considered "universal" because it may establish links with and receive EMR information from various healthcare service facilities, including those that are associated with incompatible EMRs. These EMRs, or portions of them, may ultimately be provided to one or more trusted third-party applications, such as third-party applications, 130-132.

In some cases, a linking code will be a temporary linking code. In such cases, it may be necessary to utilize the linking code to establish a link between a universal security manager and a healthcare service facility prior to a predefined expiration of the temporary linking code. The temporary linking code may provide an additional level of security for establishing a link to receive EMR information.

In other embodiments, the linking code is a permanent code such that once a link is established between the healthcare service facility and the universal security manager there is no need to establish any future links Thus, any personal information added to records of the healthcare service facility regarding the patient will be accessible to the universal security manager.

Linker 143 may utilize the linking code to establish a link for receiving medical records. For example, a healthcare service facility may be contracted with an entity associated with a universal security manager. When the healthcare service facility requests a linking code be generated from the entity associated with the universal security manager, such as in response to an interaction with an individual, the generated linking code may be known to the universal security manager. The universal security manager may also receive the linking code from a user associated with a computing device. By comparing the known linking code to the linking code received from the user via the computing device and determining that they are the same, the universal security manager may authorize receipt of EMR information, personal information stored therein, etc., for the individual from the healthcare service facility, e.g., establish a link for receiving individual's information stored at the healthcare service facility.

Using FIG. 1 as an example, after an interaction with an individual, i.e., a patient, healthcare service facility 1, 112, may request that a linking code be generated, resulting in linking code 1, 114. Linking code 1, 114, may be known to universal security manager 140 through a mutual entity (not shown) that is associated with healthcare service facility 1, 112, and universal security manager 140. Such entity could be in a contractual relationship with healthcare service facility 1, 112, and manage and/or control universal security manager 140. Further, linking code 1, 114, may be received by universal security manager 140 from a user that inputs linking code 1, 114, into computing device 160. Upon comparing the known linking code and the received linking code and determining they are the same, universal security manager 140 and/or healthcare service facility, 1, 112, may authorize medical records, or portions thereof, to be received by universal security manager 140.

In another example of establishing a link for receiving personal information at a universal security manager, a healthcare service facility may request a linking code be generated, or alternatively the linking code may be generated by the healthcare service facility. The linking code may be given to an individual in response to an interaction of the individual with the healthcare facility. In some cases, a user of a computing device may be the same as the individual that received the linking code. In some cases, the user maybe a person authorized to access or view records of the individual that received the linking code. The user may input the linking code into computing device via an input component of the computing device. The computing device may be communicatively coupled to the universal security manager, which receives the linking code from the computing device. The universal security manager may communicate the received linking code to the healthcare facility. Upon determining a match between the generated linking code and the linking code communicated by the universal security manager, the universal security manager may be authorized to receive EMRs from the healthcare facility.

Using FIG. 1 as an example, healthcare service facility 1, 112, may generate (or request to have generated) a secure linking code, resulting in linking code 1, 114. Universal security manager 140 may receive linking code 1, 114, from computing device 160, for example, using receiver 141. Upon receiving linking code 1, 114, universal security manager 140 may communicate linking code 1, 114, to healthcare service facility 1, 112, for example, via provider 144 (discussed below). In some cases, universal security manager 140 may request linking code 1, 114, from healthcare service facility 1, 112. The generated linking code 1, 114, may be compared with the received linking code 1, 114, by healthcare service facility 1, 112, and/or universal security manager 140. If the compared codes are the same, universal security manager 140 may be authorized to receive information of the individual from healthcare service facility 1, 112. Linker 143 may store information associated with authorizing universal security manager 140 to receive information from healthcare service facility 1, 112, in data storage 150. Thus, in some cases, universal security manager 140 may continually receive EMRs from healthcare service facility 1, 112, based on receiving information related to the authorization from data storage 150.

It will be appreciated that any of the methods described for authorizing a universal security manager to receive EMR information from a healthcare service facility may be repeated for other healthcare facilities and EMR systems associated therewith. For example, any of the methods may be used to authorize universal security manager 140 to receive information associated with healthcare service facility 2, 122, utilizing linking code 2, 124. Thus, many more healthcare service facilities and EMR systems and types of EMR systems may be authorized so that universal security manager 140 can receive information from the respective facilities.

Still continuing with the description of universal security manager 140, as illustrated in FIG. 1, universal security manager 140 comprises provider 144. In general, provider 144 provides information from universal security manager 140 to one or more components or entities. For example, provider 144 may communicate information utilizing a communication bus and/or a network and communicate the information to one or more healthcare service facilities, such as healthcare service facility 1, 112, and healthcare service facility 2, 122. Similarly, provider 144 may communicate information, directly or indirectly, to one or more EMR systems, such as EMR system 1, 110, and EMR system 2, 120. Note that EMR system 1 and EMR system 2 are merely exemplary and any type of personal information (e.g., an EMR, portions of information within an EMR, or other personal information of an individual) may be included in the exchange of information described herein.

The information communicated to the one or more healthcare service facilities and one or more EMRs systems may, for example, comprise linking codes, such as linking code 1, 114, and linking code 2, 124, respectively. Provider 144 may also communicate EMRs or portions thereof to third-party applications, such as third-party applications 130-132. This may include communicating requests to third-party applications to receive security standards or protocols as part of the validation process. In some case, provider 144 may communicate to trusted third-party applications all of or portions of EMRs of an individual.

In some cases, provider 144 may communicate information to computing device 160. This information may be communicated to computing device 160 in order to be provided to a user of computing device 160. For instance, information received from third-party applications, from healthcare service facilities, from EMR systems, and/or from data storage may be communicated to computing device 160 so that an output component of computing device 160 may provide the information to the user. As described above, provider 144 may provide information by way of being communicatively coupled to the one or more components or entities, such as by a bus and/or a network.

In some cases, all or portions of EMRs may be communicated by provider 144. For example, a portion of an EMR (e.g, a blood pressure value) for an individual received from healthcare service facility 1, 112, may be communicated to third-party application 130. In some cases, the information of the individual may be altered by provider 144 prior to communicating it to a third-party application. For example, information from EMR system 1, 110, may be combined with information from EMR system 2, 120, prior to communication. In some cases, either or both of the EMRs associated with EMR system 1, 110, and EMR system 2, 120, may be redacted prior to sending the EMR to a third-party application. In some cases, the combinations of information may be communicated by provider 144 based on permissions 152.

Permissions 152 generally comprises one or more parameters for performing aspects of the present technology. Permissions 152 may be stored as software code on data storage 150. In some cases, permissions 152 may comprise parameters set by a user of computing device 160. The user may use input/output components of computing device 160 to create or maintain permissions 152. In some cases, permissions 152 may comprise parameters for receiving, validating, linking, and/or providing. For instance, parameters may comprise restrictions on the information that may be received from a health service facility and/or provided to a third-party application.

For example, the user may desire to share with a third-party application and/or a universal security manager EMR information related to nutrition and weight; however, the user may not want share EMR information related to a mental health disorder with the third-party application and/or the universal security manager. In this scenario, the user may enter parameters related to the type of EMR information received or provided. In some cases, the user may wish to set parameters on the type of information provided to different third-party applications. Using a similar example, the user may wish to define parameters so that one trusted third-party application receives nutrition and weight related EMR information, while another trusted third-party application receives the mental health related EMR information. Furthermore, since the links may be established one time for prolonged use, any additional values that are obtained may be shared with the respective third-party applications associated with those types of values.

It will be appreciated that there are many combinations of parameters that may be defined by the user for receiving and providing EMR information. It would be impractical to describe an example of each and every potential scenario. As such, the examples above are not meant to be limiting in any sense, but instead, are meant only to describe the present technology. Appreciating the vast number of parameters that may be defined by the user, the inventors intend for each and every scenario whereby a user may define receiving and providing EMR information between various healthcare service facilities and third-party applications to be included within the scope of this disclosure. This may include altering one or more EMRs for a patient from one or more healthcare facilities to include or redact information related to the individual before providing it to one or more trusted third-party applications.

In some cases, permissions 152 may comprise parameters defining validating third-party applications, such as third-party applications 130-132. For example, a user may define as parameters a minimum set of security criteria for validating a third-party application to determine the third party application is a trusted third-party application. In some cases, permissions may comprise an approval for a particular third-party application to receive EMR information, e.g., a parameter that approves the particular third-party application as a trusted third-party application.

Figure 2:
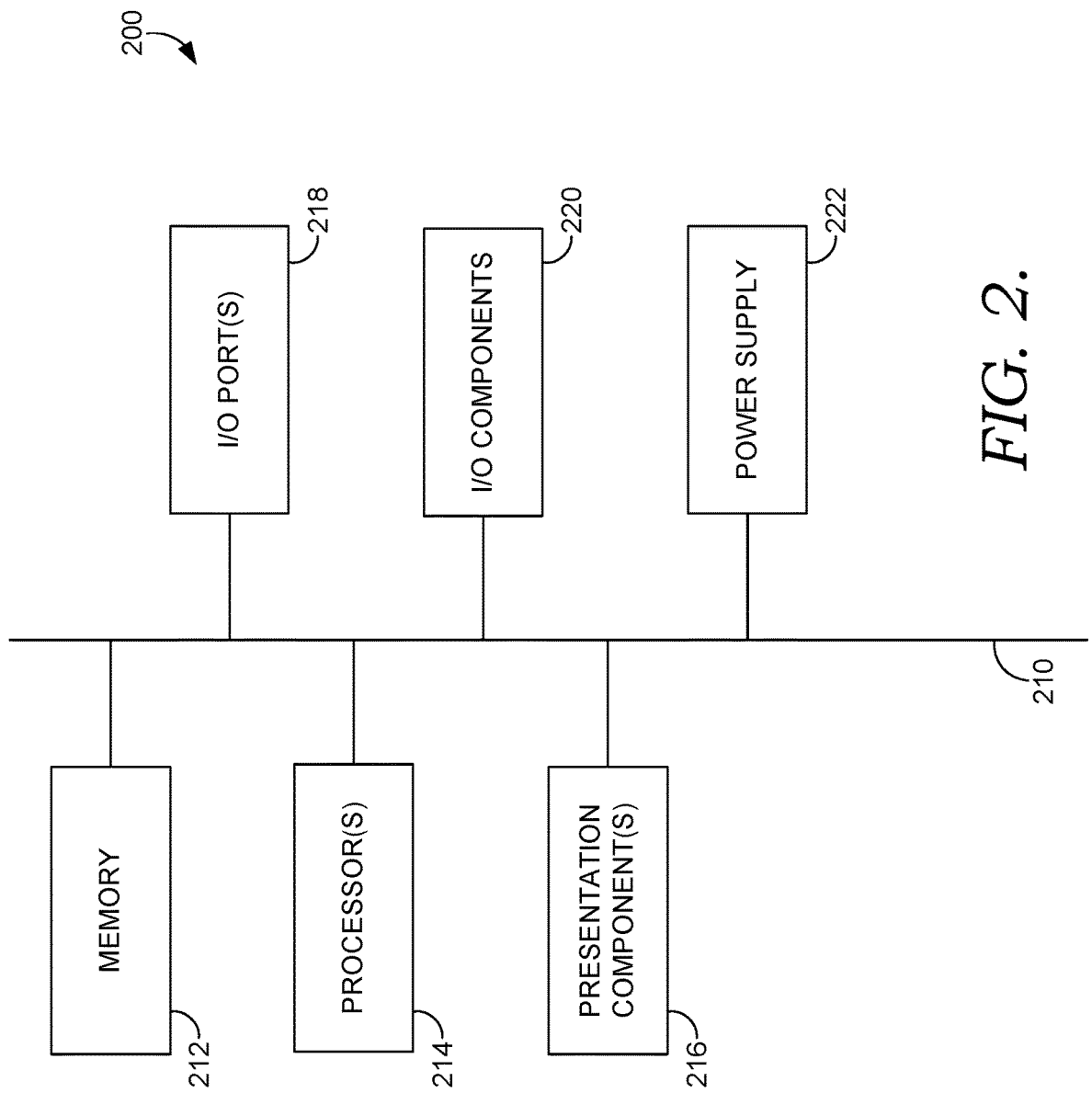
FIG. 2 is an example computing device suitable for use in embodiments of the technology, in accordance with aspects described herein.

Having described some aspects of the technology, example computing device 200 is provided in FIG. 2. Computing device 200 is one example of a suitable computing environment for practicing the technology, but is not intended to suggest any limitation as to the scope of use or functionality of the present technology. Neither should computing device 200 be interpreted as having any dependency or requirement relating to any one or combination of components illustrated.

In some cases, the technology may be described in the general context of computer code or machine-useable instructions, including computer-executable instructions such as program modules, being executed by a computer or other machine, such as a personal data assistant or other handheld device. Generally, program modules including routines, programs, objects, components, data structures, etc., refer to code that perform particular tasks or implement particular abstract data types. The technology may be practiced in a variety of system configurations, including handheld devices, consumer electronics, general-purpose computers, more specialty computing devices, etc. The technology may also be practiced in distributed computing environments where tasks are performed by remote-processing devices that are linked through a communications network.

With reference to FIG. 2, computing device 200 includes bus 210 that directly or indirectly couples the following devices: memory 212, one or more processors 214, one or more presentation components 216, input/output (I/O) ports 218, input/output components 220, and illustrative power supply 222. Bus 210 represents what may be one or more busses (such as an address bus, data bus, or combination thereof). Although the various blocks of FIG. 2 are shown with lines for the sake of clarity, in reality, delineating various components is not so clear, and metaphorically, the lines would more accurately be gray and fuzzy. For example, one may consider a presentation component such as a display device to be an I/O component. Also, processors have memory. The inventors recognize that such is the nature of the art, and reiterate that the diagram of FIG. 2 is merely illustrative of an exemplary computing device that can be used in connection with one or more embodiments of the present disclosure. Distinction is not made between such categories as "workstation," "server," "laptop," "hand-held device," etc., as all are contemplated within the scope of FIG. 2 and reference to "computing device," such as computing device 160 of FIG. 1.

With reference again to FIG. 2, computing device 200 typically includes a variety of computer-readable media. Computer-readable media can be any available media that can be accessed by computing device 200 and includes both volatile and nonvolatile media, removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 200. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 212 includes computer storage media in the form of volatile and/or nonvolatile memory. The memory may be removable, non-removable, or a combination thereof. Exemplary hardware devices include solid-state memory, hard drives, optical-disc drives, etc. Computing device 200 includes one or more processors that read data from various entities such as memory 212 or I/O components 220. Presentation component(s) 216 present data indications to a user or other device. Exemplary presentation components include a display device, speaker, printing component, vibrating component, etc.

I/O ports 218 allow computing device 200 to be logically coupled to other devices including I/O components 220, some of which may be built in. Illustrative components include a microphone, joystick, game pad, satellite dish, scanner, printer, wireless device, etc. The I/O components 220 may provide a natural user interface (NUI) that processes air gestures, voice, or other physiological inputs generated by a user. In some instance, inputs may be transmitted to an appropriate network element for further processing. A NUI may implement any combination of speech recognition, touch and stylus recognition, facial recognition, biometric recognition, gesture recognition both on screen and adjacent to the screen, air gestures, head and eye-tracking, and touch recognition associated with displays on the computing device 200. The computing device 200 may be equipped with depth cameras, such as, stereoscopic camera systems, infrared camera systems, RGB camera systems, and combinations of these for gesture detection and recognition. Additionally, the computing device 200 may be equipped with accelerometers or gyroscopes that enable detection of motion.

Turning now to FIG. 3, a block diagram of an example method 300 for establishing a universal security manager for the transfer of EMR information is provided. At block 310, a request is received from a third-party application for a first EMR (e.g., at least a portion of an EMR). In some cases, the first EMR may be stored on a first EMR system associated with a first healthcare service facility. At block 320, the third-party application is validated to determine that the third-party application is a trusted third-party application. In some cases, the third-party application may be validated based on determining that the third-party application meets a set of security criteria. In some cases, the set of security criteria is a minimum set of security criteria. In some cases, the set of security criteria is based on one or more standards defined by a rule making authority, one or more standards defined by the universal security manager, one or more standards defined by the first service facility, and/or one or more standards defined by a user.

At block 330, a first secure linking code is received. In some cases, the first secure linking code is generated at the request of the first healthcare service facility associated with the first EMR system. The first secure linking code may be generated in response to a first interaction of an individual with the first service facility. In some cases, the first linking code comprises a first unique character string. The first unique character string may be based on the first interaction of the individual with the first service facility and a first type of the first EMR system. In some cases, the interaction of the individual with the first service facility is a physical interaction at a location of the first service facility.

At block 340, the first EMR is received from the first EMR system. In some cases, this may be based on receiving the first secure linking code. At block 350, the trusted third-party application is provided with at least a portion of the first EMR. In some cases, the first EMR is provided to the trusted third-party application based on one or more permissions associated with the universal security manager. In some cases, prior to providing the trusted third-party application with the first EMR, the first EMR is altered to remove information based on the one or more permissions.

Now with reference to FIG. 4, a block diagram of another example method 400 for establishing a universal security manager for the transfer of EMR information is provided. At block 410, a request is received from a third-party application for EMR information of an individual. At block 420, the third-party application is validated to determine that the third-party application is a trusted third-party application.

At block 430, a first secure linking code is received. In some cases, the first secure linking code is generated at the request of a first service facility associated with a first EMR system. The first secure linking code may be generated in response to a first interaction of the individual with the first service facility. At block 440, a second secure linking code is received. In some cases, the second secure linking code is generated at the request of a second service facility associated with a second EMR system. The second secure linking code may be generated in response to a second interaction of the individual with the second service facility. In some cases, the second EMR system is a different type compared to the first EMR system. In some cases, the second secure linking code is different than the first secure linking code. In some cases, the first secure linking code is based on the first interaction of the individual with the first service facility and a type of first EMR system. In some cases, the second secure linking code is based on the second interaction of the individual with the second service facility and a type of second EMR system.

At block 450, a first EMR from the first EMR system and a second EMR from the second EMR system are received. At block 460, the trusted third-party application is provided the EMR of the individual based on the first EMR and the second EMR. In some cases, prior to providing the trusted third-party application with the EMR of the individual, the EMR of the individual is altered to include at least a portion of a first EMR from the first EMR system and at least a portion of the second EMR from the second EMR system.

In some cases, example method 400 may further comprise determining whether the EMR of the individual provided to the trusted third-party application is stored on the first EMR system or the second EMR system.

From the foregoing, it will be seen that this technology is one well adapted to attain all the ends and objects described above, including other advantages that are obvious or inherent to the structure. It will be understood that certain features and subcombinations are of utility and may be employed without reference to other features and subcombinations. This is contemplated by and is within the scope of the claims. Since many possible embodiments of the described technology may be made without departing from the scope, it is to be understood that all matter described herein or illustrated by the accompanying drawings is to be interpreted as illustrative and not in a limiting sense.

What is claimed is:

1. One or more non-transitory computer storage media having computer-usable instructions stored thereon, that when executed by a processor, cause the processor to perform a method for establishing a universal security manager for providing a third-party application with EMRs of an individual, the method comprising:
    receiving a request from the third-party application for a first EMR, the first EMR stored on a first EMR system;
    validating the third-party application to determine that the third-party application is a trusted third-party application;
    receiving a first secure linking code, the first secure linking code generated at the request of a first service facility associated with the first EMR system, wherein the first secure linking code is generated in response to a first interaction of the individual with the first service facility;
    based on receiving the first secure linking code, receiving the first EMR from the first EMR system; and
    providing the trusted third-party application with at least a portion of the first EMR.

2. The media of claim 1, wherein validating the third-party application comprises determining that the third-party application meets a set of security criteria.

3. The media of claim 2, wherein the set of security criteria is based on one or more standards defined by a rule making authority.

4. The media of claim 2, wherein the set of security criteria is based on one or more standards defined by the universal security manager.

5. The media of claim 2, wherein the set of security criteria is based on one or more standards defined by the first service facility.

6. The media of claim 1, wherein the first secure linking code comprises a first unique character string, wherein the first unique character string is based on the first interaction of the individual with the first service facility and a first type of the first EMR system.

7. The media of claim 1, wherein the first interaction of the individual with the first service facility is a physical interaction at a location of the first service facility.

8. The media of claim 1, wherein the first EMR is provided to the trusted third-party application based on one or more permissions associated with the universal security manager.

9. The media of claim 8, further comprising prior to providing the trusted third-party application with the first EMR, altering the first EMR to remove information based on the one or more permissions.

10. The media of claim 1, further comprising:
    receiving a request from the third-party application for a second EMR, the second EMR stored on a second EMR system, wherein the second EMR system is a different type compared to the first EMR system;
    receiving a second secure linking code, the second secure linking code generated at the request of a second service facility associated with the second EMR system, wherein the second secure linking code is generated in response to a second interaction of the individual with the second service facility;
    based on receiving the second secure linking code, receiving the second EMR from the second EMR system; and
    providing the trusted third-party application the second EMR.

11. A computer-implemented method for establishing a universal security manager for providing a third-party application with EMRs of an individual, the method comprising:
    at one or more processors, receiving a request from the third-party application for a first EMR, the first EMR stored on a first EMR system;
    at the one or more processors, validating the third-party application to determine that the third-party application is a trusted third-party application;
    at the one or more processors, receiving a first secure linking code, the first secure linking code generated at the request of a first service facility associated with the first EMR system, wherein the first secure linking code is generated in response to a first interaction of the individual with the first service facility;
    at the one or more processors, based on receiving the first secure linking code, receiving the first EMR from the first EMR system; and
    by the one or more processors, providing the trusted third-party application with the first EMR.

12. The method of claim 11, wherein validating the third-party application comprises determining that the third-party application meets a set of security criteria.

13. The method of claim 12, wherein the set of security criteria is based on one or more of (1) one or more standards defined by a rule making authority; (2) one or more standards defined by the universal security manager; and (3) one or more standards defined by the first service facility.

14. The method of claim 11, wherein the first secure linking code comprises a first unique character string, wherein the first unique character string is based on the first interaction of the individual with the first service facility and a first type of the first EMR system.

15. The method of claim 11, wherein the first EMR is provided to the trusted third-party application based on one or more permissions associated with the universal security manager, and wherein, prior to providing the trusted third-party application with the first EMR, the method comprises altering the first EMR to remove information based on the one or more permissions.

16. The method of claim 11, further comprising
    at the one or more processors, receiving a request from the third-party application for a second EMR, the second EMR stored on a second EMR system, wherein the second EMR system is a different type compared to the first EMR system;
    at the one or more processors, receiving a second secure linking code, the second secure linking code generated at the request of a second service facility associated with the second EMR system, wherein the second secure linking code is generated in response to a second interaction of the individual with the second service facility;

at the one or more processors, based on receiving the second secure linking code, receiving the second EMR from the second EMR system; and by the one or more processors, providing the trusted third-party application the second EMR.

17. The method of claim 16, wherein the second secure linking code comprises a second unique character string, wherein the second unique character string is based on the second interaction of the individual with the second service facility and the different type of the second EMR system.

18. One or more non-transitory computer storage media having computer-usable instructions stored thereon, that when executed by a processor, cause the processor to perform a method for establishing a universal security manager for providing a third-party application with EMRs of an individual, the method comprising:

receiving a request from the third-party application for an EMR of the individual;

validating the third-party application to determine that the third-party application is a trusted third-party application;

receiving a first secure linking code, the first secure linking code generated at the request of a first service facility associated with a first EMR system, wherein the first secure linking code is generated in response to a first interaction of the individual with the first service facility;

receiving a second secure linking code, the second secure linking code generated at the request of a second service facility associated with a second EMR system, wherein the second secure linking code is generated in response to a second interaction of the individual with the second service facility;

based on receiving the first secure linking code and receiving the second secure linking code, receiving a first EMR from the first EMR system and a second EMR from the second EMR system; and providing the trusted third-party application the EMR of the individual based on the first EMR and the second EMR.

19. The media of claim 18, further comprising determining whether the EMR of the individual provided to the trusted third-party application is stored on the first EMR system or the second EMR system.

20. The media of claim 18, further comprising, prior to providing the trusted third-party application with the EMR of the individual, altering the EMR of the individual to include at least a portion of a first EMR from the first EMR system and at least a portion of the second EMR from the second EMR system.

* * * * *